United States Patent [19]
Cameron

[11] Patent Number: 5,811,301
[45] Date of Patent: Sep. 22, 1998

[54] IN VITRO METHOD FOR PRODUCING DIFFERENTIATED UNIVERSALLY COMPATIBLE HUMAN BLOOD CELLS

[76] Inventor: Robert B. Cameron, 2080 Gough St., #312, San Francisco, Calif. 94109

[21] Appl. No.: 694,478

[22] Filed: Aug. 7, 1996

Related U.S. Application Data

[62] Division of Ser. No. 152,389, Nov. 16, 1993, Pat. No. 5,599,705.

[51] Int. Cl.$^6$ .............................. C12N 5/00; C12N 5/08; C12N 5/10; C12N 15/00
[52] U.S. Cl. .................. 435/372; 435/172.1; 435/172.3; 435/366; 435/372.1; 435/372.2; 435/372.3; 435/382; 435/384; 435/385; 435/386; 435/387; 435/395; 435/402; 435/403; 424/93.71; 424/93.73
[58] Field of Search .............................. 435/172.1, 172.3, 435/366, 372, 372.1, 372.2, 372.3, 382, 384, 385, 386, 387, 395, 402, 403; 424/93.71, 93.73

[56] References Cited

U.S. PATENT DOCUMENTS

| | | | |
|---|---|---|---|
| 4,721,096 | 1/1988 | Naughton et al. | 128/898 |
| 5,004,681 | 4/1991 | Boyse et al. | 435/2 |
| 5,032,507 | 7/1991 | Yu et al. | 424/93.73 |
| 5,154,921 | 10/1992 | Sager et al. | 424/93.7 |
| 5,192,553 | 3/1993 | Boyse et al. | 424/529 |
| 5,199,942 | 4/1993 | Gillis | 604/4 |
| 5,599,705 | 2/1997 | Cameron | 435/378 |

OTHER PUBLICATIONS

B. Palsson, et al., "Expansion of Human Bone Marrow Progenitor Cells in a High Cell Density Continuous Perfusion System", Bio/Technology, vol. 11, Mar. 1993, pp. 368–372.

M. Koller, et al., "Expansion of Primitive Human Hematopoietic Progenitors in a Perfusion Bioreactor System with IL–3, IL–6, and Stem Cell Factor", Bio/Technology, vol. 11, Mar. 1993, pp. 358–363.

I. Roberts, et al., "A Practical Minature Long–Term Bone Marrow Culture System for Investigating Early Myelodyspasia", Lukemia Research, vol. 16, No. 8, 1992, pp. 737–741.

T. Wang, et al., "A Continuous Perfusion Bioreactor for Long–Term Bone Marrow Culture", Ann. N.Y. Acad. Sci., 665, 1992, pp. 274–284.

C. Fraser, et al., "Proliferation of Totipotent Hematopoietic Stem Cells in vitro with Retention of Long–term Competitive in vivo Reconstituting Ability", Proc. Natl. Acad. Sci. USA, vol. 89, Mar. 1992, pp. 1968–1972.

C. Verfaillie, "Direct Contact Between Human Primitive Hematopoietic Progenitors and Bone Marrow Stroma is not Required for Long–term In Vitro Hematopoiesis", Blood, vol. 79, No. 11, 1992, pp. 2821–2826.

J. Cell Biochem. Suppl. O (16 Part F0, 135 (1992) Abstract.

Terstappen, Leukemia, vol. 6, No. 10, pp. 1001–1010, Oct. 1992.

Muench et al, Exp. Hematol., 20: 339–349, 1992.

Sardonini et al, Biotechnol. Prog., 9(2), pp. 131–137, 1993.

Koller et al, J. Cell. Biochem. Suppl., 0 (16 Part F), 135, 1992.

Srow et al, Blood 81(3): pp. 661–669, Feb. 1993.

Sonoda et al, Blood 72(4): pp. 1381–1386, 1988.

*Hematoporesis*, edited by D.W. Golde, Chapters 2–6, pp. 73–179, 1984.

Han, Hokkaida J. Med. Sci., 67 (5): 674–683, 1992.

*Primary Examiner*—David M. Naff
*Assistant Examiner*—Janet M. Kerr
*Attorney, Agent, or Firm*—Melvin Blacker

[57] ABSTRACT

In vitro production of clinically useful quantities of single species of mature, differentiated human blood cells is carried out by a method in which human pluripotent hematopoietic stem cells, preferably from a universal donor, are incubated in a bioreactor in a growth medium also containing specific combinations of recombinant human growth and maturation promoting polypeptide factors that expand stem cell cultures and promote the maturation and differentiation of stem cells into single species of erythroid, thrombocytic or granulocytic human blood cells, and harvesting the mature cells. The growth and maturation promoting polypeptides employed include SCGF, Interleukins 1,3,4,5,6, and 11, GM-CSF, M-CSF, G-CSF and EPO. Stem cells may be preliminarily genetically modified so as to remove histocompatibility or blood group antigens with which a recipient may be incompatible, or the stem cells may be genetically altered by transfection with appropriate DNA-containing vectors, prior to addition to the bioreactor. Erythrocytes prepared in large quantities by this method are also a good source of iron, in the form of iron-saturated hemoglobin, for use in iron replacement therapy.

16 Claims, 1 Drawing Sheet

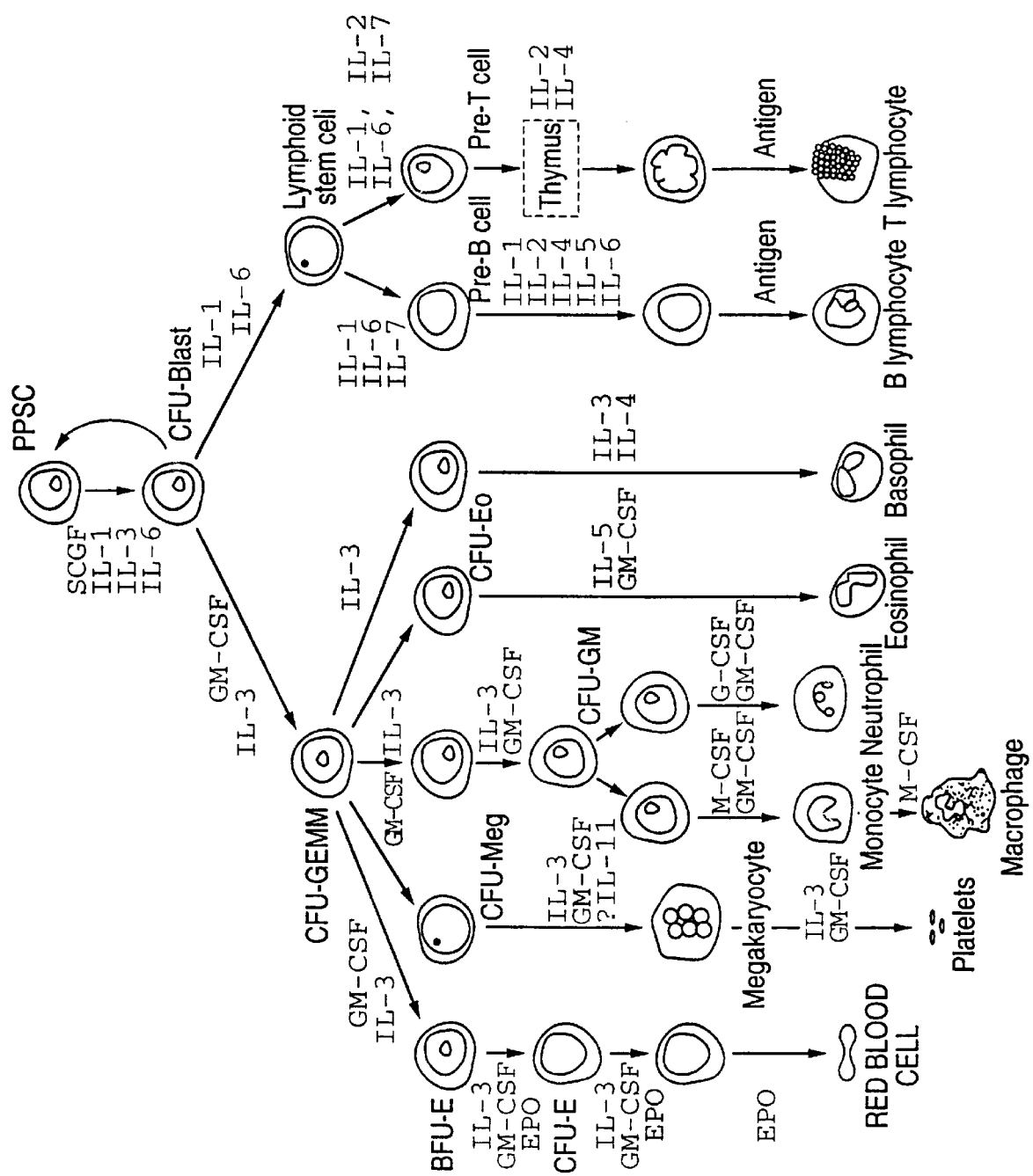

IN VITRO METHOD FOR PRODUCING DIFFERENTIATED UNIVERSALLY COMPATIBLE HUMAN BLOOD CELLS

This is a divisional of U.S. Ser. No. 08/152,389, filed Nov. 16, 1993 now Pat. No. 5,599,705, issued Feb. 4, 1997.

BACKGROUND OF THE INVENTION

1. Field of the Invention

This invention relates generally to the in vitro production of human blood cells, and more particularly to the use of recombinant human growth and maturation promoting polypeptides to produce clinically useful quantities of mature blood cells from human pluripotent hematopoietic stem cells.

2. Description of the Background Art

Despite advances in blood typing and in testing for the presence of infectious agents in blood, the use of donated human blood for transfusions remains fraught with danger. Even with typing and cross-matching, there continues to be major risks with blood transfusions including febrile or urticarial reactions (1:100), non-fatal hemolytic reactions (1:25,000) and fatal hemolytic reactions ($1:1 \times 10^6$) (Epstein, Increasing the Safety of Blood Transfusions, American Red Cross, 1992, p.1)

The other major risk of modern blood transfusion is the transmission of infectious agents. Currently, the risk of contracting HIV infection from heterologous blood transfusions has been estimated at between 1:40,000 and 1:150,000 (Epstein, 1992, above). The other major, and occasionally fatal, blood-bone infection is hepatitis, with the risk of contracting hepatitis B infections estimated at less than 1:250,000, and the risk of hepatitis C (non-A, non-B) calculated at 1:500–1:3,000 (Epstein 1992, above). Other less common but periodically significant infectious agents include HIV-2, HTLV-1 and HTLV-2 (less than $1:1 \times 10^5$), CMV (variable), Yersinia enterocolitica (less than $1:1 \times 10^6$), and rarely Trypanosoma cruz; (Chagas' disease), human parvovirus B19, Borrelia burgdorfei (Lyme disease), Treponema pallidium (syphilis), plasmodium virus and falciparum (malaria), and human herpes virus type 6 (HHV-6), (Epstein, 1992, above).

Because of these risks, there is an important need for safe alternatives for blood transfusions. Native hemoglobin has been chemically modified by various methods in an attempt to create a blood substitute, but thus far such products suffer from a variety of shortcomings, including nephrotoxicity, excessive $O_2$ affinity due to loss of 2,3-diphosphoglycerol, a short half-life (usually 4–6 hours), rapid dimerization and excretion, and insufficient plasma concentration (Skolnick *J. Amer. Med. Assoc.* 268:697 (1992); Vigerou et al., *Bull. Acad. Natl. Med.*, 174:947 (1990).

Human hemoglobin has been packaged in liposomes for administration as neo-erythrocytes, but such products are difficult to sterilize (particularly against viruses such as HIV), they exhibit a short half-life because they are rapidly cleared by the reticuloendothelial system, and significantly suppress the immune system, thereby predisposing recipients to an increased infection rate (Djordjerich et al, *Crit. Rev. Ther. Carrier Syst.*, 6:131 (1989).

Perfluorochemicals, (e.g., Fluosol-DA) have been tested as hemoglobin substitutes, but these perfluorocarbons contain a potentially toxic surfactant (Pluronic F-68), they must be stored frozen, and, due to their insolubility, require emulsification. In addition, these fluids require oxygen-enriched (potentially toxic) air for proper oxygen delivery, as well as frequent administration due to a short half-life (Skolnick, 1992 above; Vigeron, 1990, above).

It is clear that, despite these efforts, an effective and safe blood substitute is still not available. The Applicant has determined that an attractive alternate approach is, not to develop a substitute blood, but rather to produce clinically useful amounts of natural, mature, differentiated, universally compatible human blood cells under conditions such that the major risks from blood-borne infectious agents and transfusion reactions are absent to insubstantial. Such an approach has been invented, and is described below.

SUMMARY OF THE INVENTION

The invention consists of a method for in vitro culturing of pluripotent hematopoietic stem cells taken from a human donor so as to produce clinically useful amounts of a single species of infectious agent-free, universally compatible human blood cells. The stem cells are cultured in the presence of combinations of polypeptide recombinant human growth and maturation promoting factors, such as cytokines, lymphokines, colony stimulating factors, mitogens, growth factors, and maturation factors), so as to produce at will clinically useful quantities of a single species of infectious agent-free human blood cells such as erythrocytes, megakaryocytes, monocytes, macrophages, neutrophils, eosinophils, basophils, platelets, as well as expanded stem cell cultures. The human donors are preferably universal donors, i.e., blood type O, Rh factor negative.

It is an object of this invention to provide a bioreactor system, such as those containing a ceramic matrix core, hollow capillary fibers or protein coated microspheres, in order to expand the numbers of human pluripotent stem cells, by inoculating such bioreactors with human bone marrow, either in its entirety or variably purified, and subsequently perfusing the culture chamber with growth medium containing combinations of human recombinant growth and maturation promoting polypeptide factors.

It is another object of this invention to provide a method for producing in clinically useful quantities universal donor erythrocytes from universal donor stem cells expanded in a bioreactor in the presence of combinations of human recombinant growth and maturation promoting polypeptides for transfusion into patients, e.g., into anemic or thrombocytopenic patients.

It is yet another object of the invention to provide a method for the production of genetically modified human bone marrow cells techniques so as to eliminate cell surface antigens, e.g., human histocompatibility antigens and blood group antigens, such that more universal bone marrow precursor cell cultures can then be expanded for the production of universal bone marrow cells for bone marrow transplantation, as well as for the production of single species of erythrocytes, platelets, leukocytes and other mature blood cells for transfusion purposes.

Yet another object of this invention is the provision of a method of gene therapy for the treatment of congenital or acquired genetic diseases by the expansion of genetically altered bone marrow precursor cells in bioreactors until cell numbers are large enough for reinfusion into the donor patient.

It is another object of this invention to provide a method for producing large amounts of iron-heme complexes that may be collected, purified, and used as an improved source of iron for clinical administration.

These and other objects will become apparent by reference to the specification and appended claims.

DESCRIPTION OF THE FIGURES

FIG. 1 shows an overview of hematopoietic development as influenced by human growth and maturation promoting polypeptide factors.

DETAILED DESCRIPTION OF THE PREFERRED EMBODIMENTS

The Applicant has invented a combination method for expanding human hematopoietic stem cell cultures and producing from such cells clinically useful quantities of infectious agent-free, universally compatible human blood cells by culturing such bone marrow cells together with particular combinations of polypeptide human recombinant growth and maturation promoting polypeptide factors, and harvesting the thus-produced single species of human blood cells.

The expression "blood cells" is intended to include erythrocytes (red blood cells), reticulocytes, megakaryocytes, eosinophils, neutrophils, basophils, platelets, monocytes, macrophages and granulocytes. For purpose of transfusion into patients, erythrocytes, granulocytes and platelets are particularly valuable. By the expression "clinically useful quantities (or amounts) of blood cells" is intended to mean quantities of blood cells of whatever type sufficient for transfusion into human patients to treat a clinical condition.

By obtaining hematopoietic stem cells from a universal donor (i.e., blood type O, (Rh factor) negative), the cells produced according to the invention may be transfused into nearly all patients.

For the purposes of this specification and the claims, the following abbreviations and definitions will be used:

1) Hematopoiesis: The process of forming and developing the various types of circulating blood cells and blood formed elements from immature stem cells.
2) Pluripotent stem cells: primordial cells that may differentiate into various specialized types of cells.
3) Stem cell (hemocytoblast): A primitive blood cell having the ability to differentiate into cells of the granulocytes series, (e.g., promyelocytes, neutrophils, eosinophils, and basophils), the erythrocyte series (reticulocytes, erythrocytes), the thrombocyte series (megakaryoblasts, platelet-producing megakaryocytes, platelets), and the monocyte series (monocytes and macrophages).
4) Landsteiner blood groups: A, B, A/B and O (null)
5) O−: Blood devoid of types A, B or A/B, and Rh factor negative. Cells from such blood are considered universal donor blood cells as they are compatible with nearly all major blood types in recipient patients.
6) Bone marrow: A hematopoietic organ that generates billions of blood cells daily.
7) Growth and Maturation Promotinq Polypeptides ("GMPP"): Generic name for polypeptide cell growth, differentiation, and maturation promoting substances including, but not limited to, cytokines, lymphokines such as the interleukins, colony stimulating factors, mitogens, growth factors such as platelet growth factor, and differentiation factors.
8) PPSC: Pluripotent stem cell.
9) CFU-GEMM: Colony forming unit-granulocyte-erythrocyte-monocyte-megakaryocyte.
10) CFU-Meg: Colony forming unit-megakaryocyte.
11) CFU-GM: Colony forming unit-granulocyte-macrophage.
12) CFU-EO: Colony forming unit-eosinophil.
13) CFU-E: Colony forming unit-erythroid.
14) CFU-Bas: Colony forming unit-basophil.
15) GM-CSF: Granulocyte-macrophage-colony stimulating factor.
16) G-CSF: Granulocyte-colony stimulatory factor.
17) M-CSF: Macrophage-colony stimulating factor.
18) EPO: Erythropoeitin, erythrocyte maturation factor.
19) SCGF: Stem cell growth factor (also known as mast cell factor and steel factor).
20) IL-1 TO IL-11: Interleukins (lymphokines).

Most preferably, the bone marrow of adult humans of blood type O and Rh factor negative is the source of the PPSC used in the present invention.

The invention is based on the fact that the processes of hemotopoiesis from PPSC, (i.e., self-renewal), proliferation and differentiation, are controlled by specific growth and maturation promoting polypeptide substances as defined above and as abbreviated hereinafter as "GMPP". The various GMPPs act at different steps along the path to committed mature blood cells (see FIG. 1). PPSC, under the influence of SCGF, IL-1, IL-3 and IL-6, is converted to a myeloid stem cell, also referred to as CFU-blast cells. Under the additional influence of cytokines GM-CSF and IL-3, CFU-blast cells differentiate into progenitor CFU-GEMM cells. CFU-GEMM cells, under the influence of GM-CSF and IL-3 differentiate into five groups of progenitor cells namely, BFU-E (erythroid series), CFU-Meg (thrombocytic series) and CFU-GM, CFU-Eo and CFU-Bas (granulocyte series).

BFU-E, under the influence of IL-3, GM-CSF and EPO, differentiate first into CFU-E and then into mature red blood cells. CFU-Meg, under the influence of IL-3, GM-CSF and IL-11, differentiate first into platelet-forming megakaryocytes and then into mature platelets. Platelets, themselves, secrete polypeptide growth factors referred to as PDGF (platelet-derived growth factor). CFU-GM is converted to either monocytes or granulocytes under the influence of M-CSF and GM-CSF (monocytes), and G-CSF and GM-CSF (granulocytes), respectively. IL-5 and GM-CSF convert CFU-E cells into mature eosinophils. Finally, IL3 and IL-4 promote the differentiation of CFU-Bas cells into mature basophils.

According to the invention, production of clinically useful quantities of single species of red blood cells, platelets, monocyte/macrophages, neutrophils, eosinophils and basophils, as desired, is accomplished by incubating PPSC cells in a bioreactor in a controlled environment with a growth medium containing combinations of particular recombinant human GMPPs. For example, for the production of mature red blood cells, PPSC cells are contacted with the combination of SCGF, IL-1, IL-3, IL-6, and GM-CSF, and with EPO as the terminal differentiation factor. For the production of platelets, PPSC cells are incubated with a combination of SCGF, IL-1, IL-3, IL-6, GM-CSF and IL-11.

Typical protocols are described below.

Bone Marrow Preparation

As a preferred method, heparinized bone marrow is obtained by aspiration from iliac crests of a human, most preferably O−, donor by conventional surgical techniques. At the same time, one unit (500 ml) of the donor's peripheral blood is collected in ACD blood bags, and the blood stored cold for later use. Reticulum is removed from the bone marrow by filtering the marrow through a 100 micron nylon mesh. This filtered bone marrow may be used immediately without further processing. It may also be processed by conventional techniques, (e.g., Ficoll-Hypaque centrifugation, counter-current cell elutriation, monoclonal antibody-magnetic bead separations) in order to isolate general populations such as low density cells or more-purified cell populations such as CD34+, CD71-cells (see, e.g., Sutherland et al., *Blood* 74: 1563 (1989); Smeland et al. *Leukemia,* 6:845 (1992). Or, it may be preserved by incrementally freezing the bone marrow using computerized cryotechnology equipment (see U.S. Pat. Nos. 4,107,937 and 4,117,881), and storing the cells at −196° C. (liquid $N_2$).

Culture Medium

A preferred growth medium for long-term culture of bone marrow cells consists of the AIM-V medium (Gibco, Grand Island, N.Y.) supplemented with recombinant insulin (HUMULIN™, Eli Lilly & Co., Indianapolis, Ind.) at 10μg/ml, human albumin (American Red Cross, Washington, D.C.) 50mg/mL, saturated human ferritin (T5391, Sigma Chem. Co., St. Louis, Mo.) at 200 μg/mL, hydrocortisone (sodium succinate derivative, The Upjohn Co., Kalamazoo, Mich.) at $10^{-6}M$, cholesterol (C3045, Sigma Chemical Co.) at 7.5 μg/mL, and Liposyn II (10%, Abbott Labs., No. Chicago, Ill.) at 0.05 mL/mL medium. In addition, penicillin G potassium (Roerig div. of Pfizer, Inc., New York, N.Y.), gentamicin sulfate (Schering Corp., Kenilworth, N.J.) and amphotericin B (Apothecon subsidiary of Bristol-Myers-Squibb, Princeton, N.J.) are added to the cells as preservatives. Although AIM-V is preferred, other appropriate culture media may be used, such as Iscove's modified Dulbecco, Fisher's or Eagle's media. In addition, fetal calf serum or horse serum may be substituted for human serum albumin.

Recombinant SCGF (Systemix, Palo Alto, Calif.) at 10–1000 U/mL, recombinant human IL-1 (Amgen, Thousand Oaks, Calif.) at 1–100 U/mL, recombinant human IL-6 (Amgen) at 10–1000 U/ml, recombinant human IL-3 (Amgen) at 10–10,000 U/mL, and recombinant human EPO (Amgen) at 10–10,000 U/mL are added to the growth medium. In addition, recombinant human GM-CSF (Immunex, Seattle, Wash.) 1–100 U/mL is present in all cultures that are producing cells of the granulocyte series, erythrocytes series, and thrombocyte series. In addition, cultures are supplemented with recombinant human IL-5 (Arai, *Ann. Rev. Biochem,* 59:1783 (1990) at about 10–10,000 units/mL when eosinophils are to be produced, recombinant human IL-4 (Arai, above) at 10–10,000 units/mL when basophils are to be generated, and recombinant IL-11 (Genetics Institute, Boston, Mass.) at 10–10,000 units/mL when megakaryocytes and platelets are to be produced.

Boireactors

OPTICELL™ OPTICORE™ ceramic core S-51, S451 (flat surface area $23.8m^2$), S-1251 (flat surface area $10.4m^2$) or S-7251 (Cellex Biosciences, Inc., Minneapolis, Minn.) are preferred. These bioreactors are initially sterilely perfused, preferably for 1–3 days, with sterile deionized water to remove any toxic substances adhering to the core. Thereafter, the core is perfused for a brief period (less than 24 hours) with sterile 25% (w/v) human serum albumin in order to coat the core with protein. The bioreactor core is next perfused for 4–24 hours with a sterile solution of an anticoagulant, preferably heparin sulfate, 100 U/mL (Upjohn Co.) as a source of glycosaminoglycan and to prevent cell clumping during bone marrow inoculation.

Following this preparation, the core is conditioned by perfusing it with sterile human bone marrow medium (see CULTURE MEDIUM above), preferably for about 24 hours, prior to inoculating the bioreactor with bone marrow.

Bioreactor Culture System

The culture system consists of a variable number of bioreactors connected to the medium source by sterile plastic tubing. The medium is circulated through the bioreactor with the aid of a roller or centrifugal pump (e.g., KOBE™). Probes to measure pH, temperature, and $O_2$ tension are located in line at points immediately before and following the bioreactor(s). Information from these sensors is monitored electronically. In addition, provision is made for obtaining serial samples of the growth medium in order to monitor glucose, electrolytes, GMPP factors and nutrient concentrations. Activities of GMPPs are measured by conventional bioassays (e.g., bone marrow colony assays or dependent cell line growth assays) or conventional immunoassays (see, e.g., R & D Systems, Inc., Minneapolis, Minn. 55413).

Inoculation With Bone Marrow Cells

A number of bone marrow cells appropriate to the size of the bioreactor, at a concentration of about $2\times10^7$ cells/mL, are mixed with an equal volume of autologous fresh whole blood and injected into the bioreactor. Circulation of the growth medium is interrupted for a period of about 1–4 hours in order to permit the cells to attach to the surface of the bioreactor core or capillaries. Thereafter, the circulator pump is engaged and the growth medium pumped through the system at an initial rate determined by the size of the reactor; a typical rate is about 24 mL/min. Gas exchange occurs via silicone tubes (surface area=0.5 $m^2$) within a stainless steel shell, or by a conventional membrane oxygenator. $O_2$ tension and pH are monitored continuously by polarographic $O_2$ probes and autoclavable pH electrodes, respectively. Flow rates are adjusted so as to maintain an optimal $O_2$ tension (a partial pressure of at least about 30–50mm of Hg) and optimal pH (7.30–7.45).

When an appropriate number of cells has been obtained, as determined by oxygen utilization of the system, a second bioreactor may be connected to the system, and cells fed directly into this second bioreactor. Thereafter, the second bioreactor is flushed with growth medium containing a high concentration (e.g. 10,000 U/mL) of EPO or other differentiation factor, and maintained for 1–3 days for final maturation of the desired blood components.

Cell Harvesting And Processing

The bioreactor(s) is (are) mated with a conventional cell separator, and the cells are collected from the core or capillaries with gentle agitation. Harvested blood cells are processed in an automated cell separator and placed in sterile blood bags (American Red Cross) for later transfusion.

Bags of mature red blood cells are irradiated conventionally in order to inactivate any contaminating lymphocytes or other nucleated cells, and to improve sterility. Bags are refrigerated for a period of 3–5 days prior to release. During this period, the cells may be tested for undesirable contaminants, such as infectious particles.

Additional Embodiments

It is now understood that iron-saturated hemoglobin (Fe—Hb) is a good source of iron for intravenous administration to patients. The red blood cells produced according to the invention may be lysed with a hypotonic solution, and the released Fe—Hb collected sterilely and formed into complexes for intravenous use.

The system described above may also be used to expand the numbers of human pluripotent bone marrow stems cells by inoculating a bioreactor with human mononuclear bone marrow cells, either native or variably purified by conventional techniques, continuously perfusing the culture chamber with complete growth medium containing SCGF, IL-3 and IL-6, and harvesting the stem cells. By this means, bone marrow cells sufficient for human transplantation purposes may be achieved.

Culture-expanded bone marrow cells may be modified by pretreating donor cells in order to delete cell surface antigens, such as histocompatability antigens or blood group antigens. By this means, more-universal bone marrow progenitor cells for transfusion or for expansion as described above into mature blood cells may be produced. This may be accomplished, for example, by gene deletion mutations. Techniques to generate recessive loss-of-function mutations in genes by homologous recombination, targeted gene knockout and targeted integration are well known in this art (see, e.g., Rossant et al, *Phil. Trans. R. Soc. Lond. B* 339:207 (1993); Capecchi et al, *Science,* 244: 1288 (1989); Hutchinson et al, *Mutation Res.* 299:211 (1993); Galli-Taliodoros et al., *J. Immunnol. Meth.,* 181: 1 (1995)(review); Robbins, *Circ. Res.,* 73: 3 (1993) (review); Umans et al., *J. Biol. Chem.,* 270: 19777 (1995); Oancea et al., *J. Immunol.,* 155: 5678 (1995); Verneuil et al., *J. Bioenerg. Biomembr.* 27: 239 (1995); and, Brooker et al., *Letts. Applied Microbiol.,* 21: 292 (1995), all of which are incorporated by reference in their entirety. These techniques can be used to delete genes (null mutation) encoding for cell surface antigens, e.g., HLA histocompatibility and non-ABO blood group antigens, on red blood cells, platelets, and other blood cells. For example, deletion of the beta-2-microglobulin gene will prevent expression of A, B and C antigens. In a similar manner, genes for the red blood cells antigens—Kell, Kidd, and Duffy—may, if desired, also be deleted, thereby preventing the expression of their respective antigens. These techniques, when applied to progenitor stem cells, will produce individual blood cells that can be transfused into a patient without inducing antibodies which may limit further transfusions. These cells are commonly selected (after transfection) by including a second gene construct (e.g., neomycin resistance gene) that can be utilized in a positive-negative selection process (see, e.g., Mansour et al., *Nature* (Lond.) 336: 348 (1988)). The efficiency of this process may be as high as 85% (Te Riele et al, *Nature* (Lond.) 348: 649 (1990)). In addition, dominant gain of function insertion mutations may be used to treat genetic diseases that manifest symptoms due solely to enzyme or protein deficiency (see, e.g., Rossant, above; Demarquoy et al, *Experientia,* 49: 345 (1993)).

Thus, the invention can also provide single species of cells for the treatment of a wide variety of congenital or acquired genetic diseases. This is accomplished by expanding cultures of genetically altered bone marrow precursor cells in bioreactors until cell numbers are large enough for reinfusion into the patient.

What is claimed is:

1. A method for the in vitro production of a single species of differentiated universally compatible mature human blood cells, comprising the steps of:
    a) removing from a human donor pluripotent hematopoietic stem cells, wherein said human donor is a blood type O, Rh factor negative universal donor;
    b) incubating said stem cells in a bioreactor in a growth medium containing a combination of recombinant human growth or maturation promoting polypeptides, whereby said combination of polypeptides promotes the growth and differentiation of said stem cells into a desired, single species of differentiated human blood cells that are universally compatible with human recipients, said single species of blood cells being selected from the group consisting of erythroid cells, granulocytic cells, monocytic cells, thrombocytic cells, lymphocytic cells and precursors thereof; and,
    c) harvesting said single species of differentiated blood cells,
        wherein said donor stem cells are genetically modified prior to use in said bioreactor.

2. The method of claim 1, wherein said genetically modified donor stem cells are substantially free of cell surface histocompatibilty antigens that are incompatible with the recipient.

3. The method of claim 1, wherein said genetically modified donor stem cells are substantially free of cell surface blood group substances that are incompatible with the recipient.

4. The method of claim 1, wherein said genetically modified donor stem cells express an exogenous protein.

5. The method of claim 1, wherein said bioreactor comprises an artificial capillary cell culture system, a porous ceramic matrix culture system, or a protein coated microsphere culture system.

6. The method of claim 1 wherein said erythroid cells comprise erythrocytes or reticulocytes.

7. The method of claim 1, wherein said granulocytic cells comprise neutrophils, eosinophils, or basophils.

8. The method of claim 1, wherein said monocytic cells comprise monocytes or macrophages.

9. The method of claim 1, wherein said thrombocytic cells comprise megakaryocytes or platelets.

10. The method of claim 1, wherein said combination of polypeptides is selected from the group consisting of SCGF, IL-1, IL-3, IL-4, IL-5, IL-11 , GM-CSF, M-CSF, G-CSF and EPO.

11. The method of claim 10, wherein said combination of polypeptides comprises SCGF, IL-1, IL-3, IL-6, GM-CSF and EPO, and said single species of blood cells produced are erythrocytes.

12. The method of claim 10, wherein said combination of polypeptides comprises SCGF, IL-1, IL-3, IL-6, GM-CSF, and IL-11, and said single species of blood cells produced are platelets.

13. The method of claim 10, wherein said combination of polypeptides comprises SCGF, IL-1, IL-3, IL-6, GM-CSF and M-CSF, and said single species of blood cells produced are monocytes or macrophages.

14. The method of claim 1, wherein said combination of polypeptides comprises SCGF, IL-1, IL-3, IL-6, GM-CSF and G-CSF, and said single species of blood cells produced are neutrophils.

15. The method of claim 10, wherein said combination of polypeptides comprises SCGF, IL-1, IL-3, IL-6, GM-SCF and IL-5, and said single species of blood cells produced are eosinophils.

16. The method of claim 10, wherein said combination of polypeptides comprises SCGF, IL-1, IL-3, IL-6, GM-CSF, and IL-4, and said single species of blood cells produced are basophils.

* * * * *